United States Patent [19]

Ikada et al.

[11] Patent Number: 4,603,695

[45] Date of Patent: Aug. 5, 1986

[54] USE OF MOLDED POLYMERIC MATERIAL FOR PREVENTING ADHESION OF VITAL TISSUES

[75] Inventors: Yoshito Ikada; Shokyu Gen; Yasuhiko Shimizu, all of Uji; Koichi Tamura; Tatsuo Nakamura, both of Kyoto; Sosuke Kimura, Hiroshima; Tsuneo Cho, Hiroshima; Hideki Tadokoro, Hiroshima; Kazuaki Hori, Hiroshima, all of Japan

[73] Assignee: Japan Medical Supply Co., Ltd., Hiroshima, Japan

[21] Appl. No.: 626,545

[22] Filed: Jun. 29, 1984

[30] Foreign Application Priority Data

Jul. 5, 1983 [JP] Japan ................................. 58-122643

[51] Int. Cl.$^4$ ............................................. A61B 17/04
[52] U.S. Cl. ................................ 128/334 R; 128/335; 604/358; 604/364; 604/372
[58] Field of Search ........................... 128/334 R, 335; 604/358, 364, 372

[56] References Cited

U.S. PATENT DOCUMENTS

| | | | |
|---|---|---|---|
| 3,739,773 | 6/1973 | Schmitt et al. | 128/334 R X |
| 3,797,499 | 3/1974 | Schneider | 128/334 R |
| 3,875,937 | 4/1975 | Schmitt et al. | 128/334 R X |
| 3,883,901 | 5/1975 | Coquard et al. | 128/334 R X |
| 4,032,993 | 7/1977 | Coquard et al. | 128/334 R X |
| 4,208,511 | 6/1980 | Shalaby et al. | 128/334 R X |
| 4,343,931 | 8/1982 | Barrows | 128/334 R X |
| 4,429,080 | 1/1984 | Casey et al. | 128/334 R X |
| 4,490,326 | 12/1984 | Beroff et al. | 128/334 R X |
| 4,523,591 | 6/1985 | Kaplan et al. | 128/334 |

*Primary Examiner*—Lucille M. Phynes
*Attorney, Agent, or Firm*—Kramer and Brufsky

[57] ABSTRACT

An adhesion preventive for preventing adhesion between vital tissues is provided. The present adhesion preventive is a molded material consisting essentially of a biodegradable and absorbable polymer. It has an advantage of requiring no reoperation for its removal since it would be degraded and absorbed after completing its function in vivo.

20 Claims, No Drawings

USE OF MOLDED POLYMERIC MATERIAL FOR PREVENTING ADHESION OF VITAL TISSUES

BACKGROUND OF THE INVENTION

This invention relates to an adhesion preventive. More particularly, it relates to a material useful in surgical operations for preventing adhesion of vital tissues such as skin, blood vessels or organs.

Vital tissues such as blood vessels or organs including kidney, liver and intestines are coated with mucous membranes or serous membranes so that they can function independent of each other. For example, there are body wall pleura and organ pleura in the thoracic cavity and parietal peritoneum and mesentery in the abdominal cavity, each protecting the corresponding organs. Surgical operations or inflammation in those portions of the body coated with serous membranes could result in adhesion regardless of the size of the affected part. Such adhesion between vital tissues may be observed not only in particular portions of the body but in all vital tissues. Adhesion between vital tissues has heretofore presented a serious problem in the surgical field.

In the field of orthopedics, acute or chronic arthritis such as suppurative, gonorrheal, tuberculous or rhemumatoid arthritis or traumatic injuries at a joint such as fracture or sprain would result in ankylotic diseases wherein the surface of the bones constituting the joint adhere to each other and thereby restrict the mobility of the joint. Congenital radioulnar synostosis wherein a spoke bone and an ulna adhere together at the proximity is difficult to remedy by a surgical operation, since the separated bones would frequently readhere.

When neural spine and spinal cord are removed dorsally by a surgical operation in a vertebral canal cavity in treating myeloma, hernia of intervertebral or adhesive spinal meningitis, it is necessary to prevent adhesion to the body wall. Further, suturing of ruptured tendons and tendon transfer would sometimes fail because of the postoperative adhesion of the tendon to the scar in the skin. Furthermore, in the case of rupture of a flexor tendon between a metacarpophalangeal joint and a proximophalangeal joint, the function of the finger would not recover by the intermittent suture of musculus flexor digitorum superficialis and musculus flexor digitorum profundus since these tendons injured simultaneously would adhere to each other. Therefore, it is also necessary to prevent adhesion between the two tendons in this case.

In the field of thoracosurgery, bronchi dilated by primary diseases such as pulmonary or suppurative diseases would allow the extension of inflammation over the surrounding pulmonary parenchyma and the formation of suppurative focus to thereby result in adhesion to pleura. In addition, lung cancer would result in adhesion of a focus to the body wall.

In the field of abdosurgery, external damages such as disjunction or rupture by a severe impact or morbid damages such as inflammation or tumor in organs in an abdominal cavity including liver, kidney, pancreas, spleen and intestine would result in adhesion of organs to each other or of an organ to the abdominal wall. Rupture of the diaphragm or peritoneum caused by a severe external closed damage would result in adhesion of an organ to the abdominal wall. Further, ileus of the small or, large intestine, which has the same meaning as intestinal obstruction and generally refers to an acute obstruction, would be mainly caused by adhesive ileus wherein the intestinal cavity is closed by a crooked or flexed intestinal tract resulting from adhesion in the abdominal cavity most of which would be formed postoperatively. Therefore, it is necessary to prevent adhesion in the abdominal cavity after the operation to prevent said adhesive ileus. Abdominal abscess could sometimes result in adhesion of peritoneum, diaphragm or pleura to each other. In addition, adhesion between adjacent organs or of an organ to the abdominal wall should be prevented in the case of various diseases or tumors which cannot be removed completely in internal organs.

In the fields of obsterics and gynecology, endometritis, excessive artificial abortions or intrauterine curettage would sometimes result in partial or whole adhesion of placenta to uterine wall, which makes separation of the placenta at delivery difficult. Furthermore the primary focus of breast cancer would multiply remarkably to thereby adhere to skin or a tendon.

In the field of brain surgery, adhesive arachnitis would be induced by chronic or suppurative intracranial inflammation resulting from an unknown primary cause, syphilis, tuberculosis, or the like, a sequela of an external damage in head, intrahecal injection of medicine in therapy, or myelography.

In addition, adhesion resulting from facial palsy which is caused by a malignant tumor in the salivary gland would sometimes restrict mobility. A cervical lymph node timefied by transfer of cancer would consolidate and adhere to the surrounding tissues to thereby restrict mobility.

As described above, adhesion of vital tissues, large or small, may be observed in most of the surgical fields. Adhesion could occur for various reasons including mechanical and chemical stimulations of vital tissues accompanying surgical operations, postoperative bacterial infection, inflammation or complications. Consequently, it is necessary to prevent postoperative adhesion between vital tissues.

Conventional adhesion preventives such as liquid paraffin, camphor oil, chondroitin sulfuric acid and urea exhibit an insufficient effect since they function only temporarily. On the other hand, polymer membranes such as gutta percha or poly(tetrafluoroethylene), which have been used for preventing postoperative adhesion at portions of the body where there is a fear of adhesion setting in, would remain in the body as foreign bodies. Therefore, it is desirable to take out the used membrane by reoperation.

SUMMARY OF THE INVENTION

It is an object of the present invention to provide a material capable of completely preventing adhesion. It is another object of the present invention to provide an adhesion preventive which requires no reoperation for its removal. It is a further object of the present invention to provide an adhesion preventive which can be used safely in surgery performed on warm blooded mammals.

The adhesion preventive of the present invention is a molded material comprising a polymer which is absorbable by degradation in vital tissues. The adhesion preventive comprises a polymer which is biodegradable and absorbable and preferably has a half-life period by weight from seven days to one year in vivo. Therefore, it is possible to prevent adhesion by placing the adhesion preventive at that portion of the body of a warm blooded mammal undergoing surgery where there is a fear of adhesion setting in for a period depending on the rate of absorption by degradation. Then the adhesion preventive would be absorbed and disappear without requiring reoperation for its removal.

DETAILED DESCRIPTION OF THE INVENTION

The biodegradable and absorbable polymer to be used as the adhesion preventive of the present invention is generally one of those polymer materials which would be absorbed by hydrolysis in vivo. Examples of these polymer materials include polyesters obtained by polymerizing various hydroxycarboxylic acids, lactones or the like, collagen, amino acid polymers and chitin. Among them, it is preferable to use those having a half-life period by weight from seven days to one year by degradation and absorption in vivo.

More particular examples of polyesters are those represented by the following repeating units (I), (II), (III) and (IV):

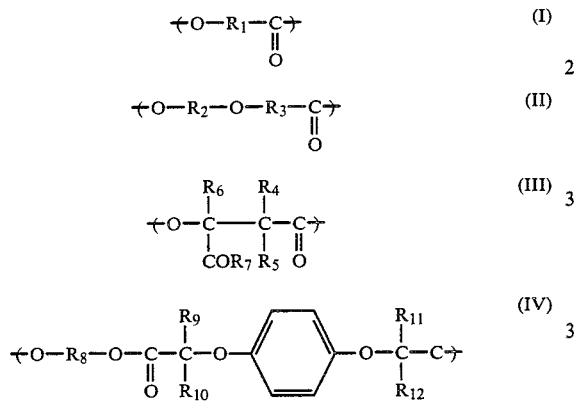

wherein $R_1$, $R_2$, $R_3$ and $R_8$ each represent a $C_1$ to $C_{10}$ divalent alkylene group with or without substituent(s); $R_4$, $R_5$, $R_6$, $R_9$, $R_{10}$, $R_{11}$ and $R_{12}$ represent each a hydrogen atom or a lower alkyl group; and $R_7$ represents $OR_7'$ or $NR_7''R_7'''$ wherein $R_7'$, $R_7''$ and $R_7'''$ each represent a hydrogen atom or a lower alkyl group.

Examples of polyesters represented by the formula (I) include those obtained from glycolic acid, lactic acid, β-hydroxybutylcarboxylic acid, β-propiolactone, γ-butyrolactone, γ-valerolactone, δ-caprolactone, ε-caprolactone and methyl-ε-caprolactone. Examples of polyesters represented by the formula (II) include those obtained from p-dioxanone, methyl-p-dioxanone and dimethyl-p-dioxanone. Examples of polyesters represented by the formula (III) include those obtained by ring opening polymerization of β-malolactone which is prepared by the esterification or amidation of malic acid, citramalic acid, citric acid or the like. Examples of polyesters represented by the formula (IV) include those obtained by polymerizing alkylene glycols such as ethylene glycol, propylene glycol or butylene glycol with phenylenebisoxyacetate. These polyesters may be homopolymers or copolymers obtained by copolymerizing any other components without departing from the spirit of the present invention.

These polyesters may be prepared by well-known methods. That is, polymers having the repeating units represented by the formulae (I), (II) or (III) may be obtained by dehydration polycondensation of hydroxycarboxylic acids or ring-opening polymerization of cyclic dimers, lactones, dioxanones or β-malolactone in the presence of a metal catalyst. Polymers represented by the formula (IV) may be obtained by transesterification of an alkylene glycol and phenylenebisoxyacetate in the presence of a catalyst followed by polycondensation thereof.

Among the aforementioned polymers, a homopolymer of lactic acid or a copolymer containing at least 50 mole % of lactic acid units may be most desirable. Lactic acid, which is a product of decomposition of these polymers, is harmless since it would supply energy in vivo and be introduced into the normal metabolic pathways. Consequently, these polymers may be used safely as an adhesion preventive. In addition, these polymers exhibit quite suitable degradation and absorption rates as an adhesion preventive. It is preferable to copolymerize glycolic acid with lactic acid. The degradation and absorption rate of the copolymer of glycolic acid and lactic acid would increase with an increase in the glycolic acid content. Therefore, it is possible to obtain a polymer exhibiting the optimal degradation and absorption rate for each case by adjusting the glycolic acid content thereof. It is further possible to obtain a polymer exhibiting the desired degradation and absorption rate by adjusting the degree of polymerization thereof. That is, the degradation and absorption rate of the polymer would increase with a decrease in the degree of polymerization and vice versa.

The molecular weight of the biodegradable and absorbable polymer for use in the present invention preferably can range from 1,000 to 1,000,000.

The adhesion preventive of the present invention is generally used in the form of a sheet of a desired size and shape. In addition, it may be processed to obtain not only non-porous films or sheets but any desired products such as porous, fabric or knitted films or sheets. These products may be readily prepared by well-known processes such as molding or solution casting. The thickness of the adhesion preventive is preferably from 10 to 1,000 μ.

It is possible to prevent adhesion conveniently and completely by inserting the adhesion preventive of the present invention at that portion of the body of the warm blooded mammal where there is a fear of adhesion setting in. Furthermore, the adhesion preventive of the present invention would be gradually degraded and absorbed in vivo so that it is not necessary to take it out by reoperation thereby differing from gutta percha or poly(tetrafluoroethylene).

The adhesion preventive of the present invention can be sterilized by ethylene oxide gas, γ-rays or electron beams prior to use.

The following examples further illustrate the present invention. These examples are for illustrative purposes only and are not to be construed as imposing any limitations upon the spirit or scope of this invention. Unless otherwise stated, all percentages and parts are by weight.

EXAMPLE 1

In the presence of 0.03% by weight of tin octoate and 0.1% by weight of lauryl alcohol, D,L-lactide which was a cyclic condensate of D,L-lactic acid was allowed to react for three hours at 160° C. under reduced pressure of $10^{-3}$ mmHg to prepare a lactic acid polymer having a molecular weight of 42,000. The polymerization yield of the polymer determined by thermogravimetric analysis was 98%. The obtained polymer containing 2% of residual monomer was dissolved in acetone to prepare a polymer solution. Then a film of 100 μ in thickness was prepared from the polymer solution. The glass transition point of the film was 51° C.

Approximately 0.6 g of the film was introduced into 20 ml of a PBS buffer solution and subjected to a hydrolysis test in vitro in a thermostatic chamber equipped with a vibrator. No change was observed for a week. The sample began to swell and became opaque after 10 days without any decrease in weight. The weight of the sample began to decrease after four weeks. The sample was completely hydrolyzed and had no trace of the original after approximately five months.

Then a sample (2 cm ×2 cm) prepared from the aforementioned film was buried in dorsal subcutaneous tissue (above the dorsal fascia) of rabbits under sterile conditions. Then the treated parts of the rabbits sacrificed after three days, five days, a week, two weeks, 10 weeks and 20 weeks were cut open to observe the samples. Patholohistologic examination on the surrounding tissues in contact with the samples were also carried out. No change was observed with the naked eye in the sample obtained one week after the treatment. The sample obtained two weeks after the treatment was opaque on the whole and exhibited similar mechanical strength as before the treatment. The sample could not be found in the rabbit sacrificed 20 weeks after the treatment since it was completely absorbed in vivo. Neither inflammation nor vascular hyperplasia was observed in each case.

These results suggest that the hydrolysis test in vitro would approximately correspond to the degradation and absorption in vivo. They also suggest that the aforementioned film would be preserved for several weeks in vivo thereby preventing adhesion and then absorbed rapidly. In addition, it has been confirmed that the film is compatible with warm blooded mammals and excellent as an adhesion preventive.

EXAMPLE 2

D,L-Lactide and glycolide, which is a a cyclic condensate of glycolic acid, were reacted at various rates as shown in the following table in the same manner as in Example 1 to obtain lactic acid/glycolic acid copolymers having various compositions. Each copolymer thus obtained was formulated into a sheet of 100μ in thickness by molding with a hot press.

| No. | D,L-Lactide content in monomer (% by weight) | Polymerization degree (%) | Glass transition point (°C.) |
|---|---|---|---|
| LA-75 | 75 | 97 | 39 |
| LA-50 | 50 | 98 | 34 |
| LA-25 | 25 | 96 | 35 |

In vitro hydrolysis tests were carried out on these films in a similar manner as in Example 1. Consequently, it was found that approximately 20% by weight of LA-75, approximately 40% by weight of LA-50 and approximately 60% by weight of LA-60 were lost within four weeks, respectively. These results suggest that the hydrolysis rate of the copolymers would increase with a decrease in the lactic acid content.

Then, the same in vivo test as in Example 1 was carried out. By observing samples obtained one week and 20 weeks after the treatment, it was found that all of the former samples were opaque and the brittleness of them would increase with a decrease in the lactic acid content, while none of the latter samples were found since all of them had disappeared by absorption. No inflammation nor vascular hyperplasia was observed in each case.

These results indicate that it is possible to obtain a lactic acid/glycolic acid copolymer having the optimal degradation and absorption rate by adjusting the composition of the copolymer.

EXAMPLE 3

75% by weight of D,L-lactide and 25% by weight of ε-caprolactone were reacted under the same conditions as in Example 1 to prepare lactic acid/ε-caprolactone copolymer. The polymerization yield of the polymer was 97%. The obtained polymer was dissolved in acetone and formulated into a film of 50μ in thickness by casting. The glass transition point of the film was −5° C.

Then the same hydrolysis test in vitro as in Example 1 was carried out. No change was observed for the first three weeks. The sample became opaque on the whole after one month, accompanied by no decrease in weight. The sample began to decrease in weight after two months and was completely degraded after one year.

The same in vivo test as in Example 1 was carried out. By observing samples obtained 10 weeks and one year after the treatment, it was found that the former samples were opaque on the whole, while the latter samples were degraded and completely absorbed. No inflammation nor vascular hyperplasia was observed in each case.

What is claimed is:

1. A method for preventing adhesion between vital tissues which comprises placing between said tissues a molded material consisting essentially of a biodegradable and absorbable polymer selected from the group consisting of a polyester having repeating units of the formula:

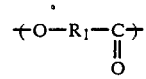

in which $R_1$ represents a $C_1$ to $C_{10}$ divalent alkylene group, a polyester having repeating units of the formula:

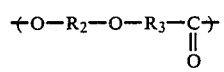

in which each of $R_2$ and $R_3$ represents a $C_1$ to $C_{10}$ divalent alkylene group, a polyester having repeating units of the formula:

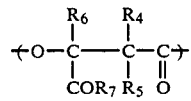

in which each of $R_4$, $R_5$, and $R_6$ represents hydrogen or a lower alkyl group, and $R_7$ represents $OR_7'$ or $NR_7''R_7'''$ in which each of $R_7'$, $R_7''$ and $R_7'''$ represents hydrogen or a lower alkyl group, a polyester having repeating units of the formula:

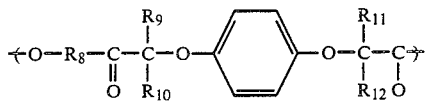

in which $R_8$ represents a $C_1$ to $C_{10}$ divalent alkylene group, and each of $R_9$, $R_{10}$, $R_{11}$ and $R_{12}$ represents hydrogen or a lower alkyl group, collagen, an amino acid polymer or chitin.

2. A method according to claim 1 in which the polymer is a polyester having repeating units of the formula:

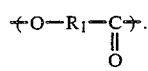

3. A method according to claim 2 in which the polyester is a lactic acid homopolymer.

4. A method according to claim 2 in which the polyester is a lactic copolymer.

5. A method according to claim 4 in which the polyester is a copolymer of lactic acid and glycolic acid.

6. A method according to claim 4 in which a lactic acid copolymer contains at least 50 mole % of lactic acid.

7. A method according to claim 1 in which the polymer is a polyester having repeating units of the formula:

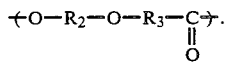

8. A method according to claim 7 in which the polyester is a homopolymer or a copolymer of a p-dioxanone.

9. A method according to claim 1 in which the polymer is a polyester having repeating units of the formula:

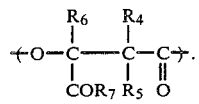

10. A method according to claim 1 in which the polymer is a polyester having repeating units of the formula:

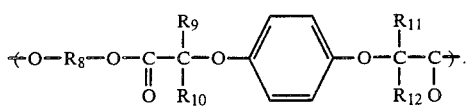

11. A method according to claim 1 in which the polymer is collagen.

12. A method according to claim 1 in which the polymer is an amino acid polymer.

13. A method according to claim 1 in which the polymer is chitin.

14. A method according to claim 1 in which the molded material is in the form of a sheet.

15. A method according to claim 14 in which the sheet is from 10 to 1,000 microns in thickness.

16. A method according to claim 14 in which the sheet is non-porous.

17. A method according to claim 14 in which the sheet is porous.

18. A method according to claim 14 in which the sheet is a fabric or a knit.

19. A method according to claim 1 in which the polymer has a molecular weight of from 1,000 to 1,000,000.

20. A method according to claim 1 in which the polymer has a half-life period by weight ranging from seven days to one year as the result of degradation and absorption in vivo.

* * * * *

UNITED STATES PATENT AND TRADEMARK OFFICE
CERTIFICATE OF CORRECTION

PATENT NO. : 4,603,695
DATED : August 5, 1986
INVENTOR(S) : Ikada, et al

It is certified that error appears in the above-identified patent and that said Letters Patent is hereby corrected as shown below:

IN THE SPECIFICATIONS:

At Column 3, formula (IV) of the Patent, change:

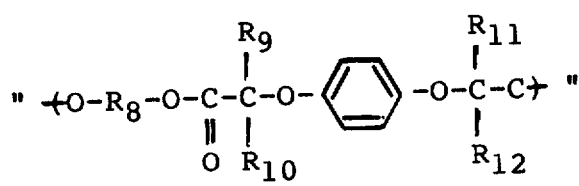

to

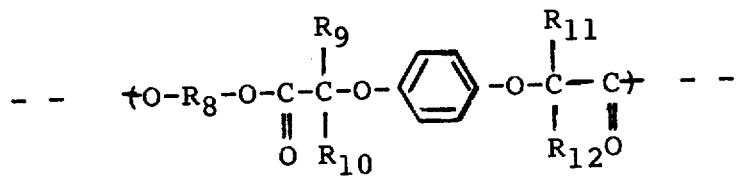

UNITED STATES PATENT AND TRADEMARK OFFICE
CERTIFICATE OF CORRECTION

PATENT NO. : 4,603,695
DATED : August 5, 1986
INVENTOR(S) : Ikada, et al

It is certified that error appears in the above-identified patent and that said Letters Patent is hereby corrected as shown below:

IN THE CLAIMS:

In claim 1, column 7, line 5 of the Patent, change:

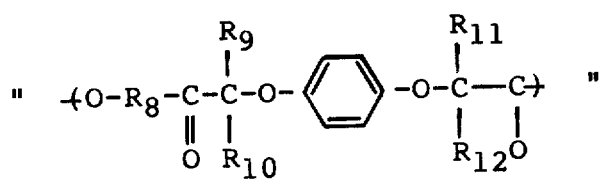

to

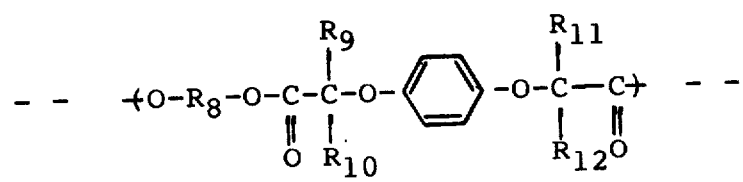

In claim 4, column 7, line 25, change "lactic copolymer" to -- lactic acid copolymer --.

UNITED STATES PATENT AND TRADEMARK OFFICE
CERTIFICATE OF CORRECTION

PATENT NO. : 4,603,695
DATED : August 5, 1986
INVENTOR(S) : Ikada, et al

It is certified that error appears in the above-identified patent and that said Letters Patent is hereby corrected as shown below:

In Claim 10, column 8, line 15 of the Patent, change:

" 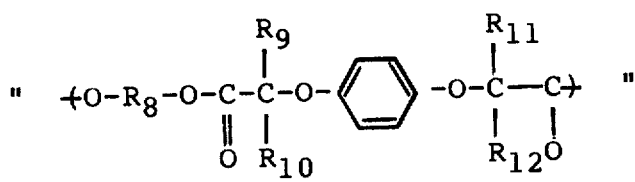 "

to

-- 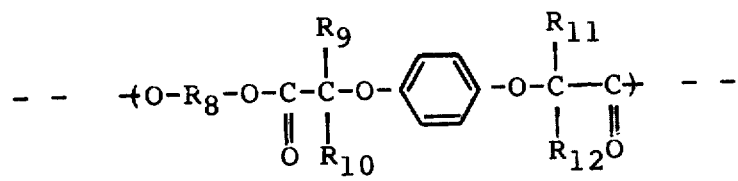 --

Signed and Sealed this

Fourth Day of November, 1986

[SEAL]

Attest:

DONALD J. QUIGG

Attesting Officer

Commissioner of Patents and Trademarks